(12) United States Patent
Takahashi et al.

(10) Patent No.: US 12,180,440 B2
(45) Date of Patent: Dec. 31, 2024

(54) MICROCHIP AND SAMPLE SORTING KIT

(71) Applicant: SONY CORPORATION, Tokyo (JP)

(72) Inventors: Kazuya Takahashi, Tokyo (JP); Yoichi Katsumoto, Tokyo (JP)

(73) Assignee: SONY CORPORATION, Tokyo (JP)

( * ) Notice: Subject to any disclaimer, the term of this patent is extended or adjusted under 35 U.S.C. 154(b) by 957 days.

(21) Appl. No.: 17/057,955

(22) PCT Filed: May 21, 2019

(86) PCT No.: PCT/JP2019/020025
§ 371 (c)(1),
(2) Date: Nov. 23, 2020

(87) PCT Pub. No.: WO2019/230489
PCT Pub. Date: Dec. 5, 2019

(65) Prior Publication Data
US 2021/0189309 A1 Jun. 24, 2021

(30) Foreign Application Priority Data
Jun. 1, 2018 (JP) ................................. 2018-106180

(51) Int. Cl.
*B01L 3/00* (2006.01)
*C12M 1/26* (2006.01)
(Continued)

(52) U.S. Cl.
CPC .............. *C12M 1/26* (2013.01); *G01N 35/08* (2013.01); *G01N 37/00* (2013.01)

(58) Field of Classification Search
CPC ......... B01L 3/502715; B01L 3/502776; B01L 3/502784; B01L 2200/0652;
(Continued)

(56) References Cited

U.S. PATENT DOCUMENTS 6,432,630 B1 * 8/2002 Blankenstein .......... B03C 1/035
436/514
6,599,436 B1 7/2003 Matzke et al.
(Continued)

FOREIGN PATENT DOCUMENTS

CN 101109762 A 1/2008
CN 101581728 A 11/2009
(Continued)

OTHER PUBLICATIONS

International Search Report and Written Opinion of PCT Application No. PCT/JP2019/020025, issued on Aug. 20, 2019, 10 pages of ISRWO.
(Continued)

*Primary Examiner* — Jill A Warden
*Assistant Examiner* — Dwayne K Handy
(74) *Attorney, Agent, or Firm* — CHIP LAW GROUP (57) ABSTRACT

A technology capable of preventing a sample from being retained is to be provided. Provided are a microchip that includes at least a sample inlet into which a sample is introduced, a sample flow path through which the sample introduced from the sample inlet flows, and a sorting flow path in which a target sample is sorted out from the sample, in which a first tube is inserted into and fixed to the sample inlet, and a sample sorting kit that includes at least the microchip.

17 Claims, 5 Drawing Sheets

(51) Int. Cl.
*G01N 35/08* (2006.01)
*G01N 37/00* (2006.01)

(58) Field of Classification Search
CPC .. G01N 15/1484; G01N 35/08; G01N 35/085; G01N 2015/1486; G01N 15/149; G01N 15/1492
See application file for complete search history.

(56) References Cited

U.S. PATENT DOCUMENTS

| | | |
|---|---|---|
| 2004/0201174 A1 | 10/2004 | Dodgson et al. |
| 2005/0109410 A1* | 5/2005 | Gilbert ................ F16K 99/0036 137/827 |
| 2008/0031790 A1 | 2/2008 | Ohta et al. |
| 2010/0315639 A1 | 12/2010 | Muraki |
| 2011/0177547 A1 | 7/2011 | Xia |
| 2011/0271746 A1 | 11/2011 | Shinoda |
| 2012/0153185 A1 | 6/2012 | Ito et al. |
| 2015/0203416 A1* | 7/2015 | Van Dam .......... B01L 3/502784 536/122 |
| 2018/0104691 A1 | 4/2018 | Merten et al. |
| 2019/0071630 A1 | 3/2019 | Saakuma et al. |

FOREIGN PATENT DOCUMENTS

| | | |
|---|---|---|
| CN | 101923036 A | 12/2010 |
| CN | 102564925 A | 7/2012 |
| CN | 107051911 A | 8/2017 |
| EP | 3072595 A1 | 9/2016 |
| JP | 2002-048752 A | 2/2002 |
| JP | 2005-274199 A | 10/2005 |
| JP | 2007-108075 A | 4/2007 |
| JP | 2008-023406 A | 2/2008 |
| JP | 2009136789 A | 6/2009 |
| JP | 2010-286292 A | 12/2010 |
| JP | 2012-127922 A | 7/2012 |
| JP | 2017-058375 A | 3/2017 |
| WO | WO-2002023163 A1 | 3/2002 |
| WO | 2012/007182 A1 | 1/2012 |
| WO | 2017/159422 A1 | 9/2017 |

OTHER PUBLICATIONS

Office Action for CN Patent Application No. 201980035017.1, issued on Sep. 16, 2024, 02 pages of English Translation and 02 pages of Office Action.

* cited by examiner

MICROCHIP AND SAMPLE SORTING KIT

CROSS REFERENCE TO RELATED APPLICATIONS

This application is a U.S. National Phase of International Patent Application No. PCT/JP2019/020025 filed on May 21, 2019, which claims priority benefit of Japanese Patent Application No. JP 2018-106180 filed in the Japan Patent Office on Jun. 1, 2018. Each of the above-referenced applications is hereby incorporated herein by reference in its entirety.

TECHNICAL FIELD

The present technology relates to a microchip and a sample sorting kit.

BACKGROUND ART

Currently, a technology called flow cytometry is used for analyzing microparticles such as cells and microorganisms. The flow cytometry is an analysis method for performing an analysis, sorting, and the like of microparticles by irradiating, with light, the microparticles that are flowing in such a way as to be included in a sheath flow delivered to a flow path, and detecting the fluorescence and the scattered light emitted from the individual microparticles. An apparatus used for the flow cytometry is called a flow cytometer.

The flow cytometer employs a microchip that includes a silicon or glass substrate on which an area for conducting chemical or biological analyses and flow paths are provided. An analysis system equipped with such a microchip is called a micro-total-analysis system (μ-TAS), a lab-on-a-chip, a biochip, or the like.

Examples of application of μ-TAS to the microparticle measuring technology include a microparticle sorting apparatus that optically, electrically, or magnetically measures the characteristics of microparticles in a flow path or an area disposed on a microchip to sort the microparticles. Such a flow cytometer (microchip-type flow cytometer) to which μ-TAS is applied is advantageous in that cross contamination of samples between measurements can be prevented by constructing a flow path system in a microchip, for example.

For example, Patent Document 1 discloses "a microchip including: a main flow path through which a fluid that contains microparticles flows; and a sorting flow path in which a capturing chamber where the microparticles are taken and a pressure chamber where a negative pressure is generated are disposed, the sorting flow path communicating with the main flow path, in which cross sections of the capturing chamber and the pressure chamber, the cross sections being perpendicular to the flow direction of the fluid, are formed to be larger than a cross section of any other portion of the sorting flow path, the cross section being perpendicular to the flow direction of the fluid".

CITATION LIST

Patent Document

Patent Document 1: Japanese Patent Application Laid-Open No. 2017-058375

SUMMARY OF THE INVENTION

Problems to be Solved by the Invention

Conventional microchips employ a structure in which the microchip is connected to an external flow path via a manifold. However, this structure is problematic in that a sample is retained in a flow path.

Therefore, a main object of the present technology is to provide a technology capable of preventing samples from being retained.

Solutions to Problems

First of all, a microchip is provided in the present technology, the microchip including at least: a sample inlet into which a sample is introduced; a sample flow path through which the sample introduced from the sample inlet flows; and a sorting flow path in which a target sample is sorted out from the sample, in which a first tube is inserted into and fixed to the sample inlet.

In the microchip according to the present technology, the first tube may be fixed coaxially with the sample flow path.

Furthermore, in the microchip according to the present technology, the first tube may be fixed with an adhesive agent. In this case, the sample inlet may be provided with an abrupt expansion flow path having a larger volume than the volume of the sample flow path. Furthermore, in this case, the volume of the abrupt expansion flow path may be equal to or greater than $\pi\varphi^2 L/4$ m$^3$, where $\varphi$ is an outer diameter of the first tube and L is a length of the first tube. Moreover, in this case, the abrupt expansion flow path may be provided upstream of an end of the sample inlet, the end being on a side where the first tube is fixed.

Furthermore, in the microchip according to the present technology, an end of the sample inlet, the end being on a side where the first tube is fixed, and an end of the first tube, the end being on a side where the first tube is fixed to the sample inlet, may be tapered.

In addition, in the microchip according to the present technology, a second tube may be further fixed to an end of the first tube, the end being on a side where the first tube is not fixed to the sample inlet.

Furthermore, in the microchip according to the present technology, a third tube may be inserted into and fixed to an outlet of the sorting flow path.

Moreover, the microchip according to the present technology may further include a disposal flow path through which a sample other than the target sample is discarded, and a fourth tube may be inserted into and fixed to an outlet of the disposal flow path.

In addition, the microchip according to the present technology may further include: a sheath fluid inlet into which a sheath fluid is introduced; and a sheath flow path through which the sheath fluid introduced from the sheath fluid inlet flows, and a fifth tube may be inserted into and fixed to the sheath fluid inlet.

Furthermore, the microchip according to the present technology may further include: a gate fluid inlet into which a gate fluid is introduced; and a gate flow path through which the gate fluid introduced from the gate fluid inlet flows, and a sixth tube may be inserted into and fixed to the gate fluid inlet.

Furthermore, in the present technology, a sample sorting kit is also provided, the sample sorting kit including at least: a containing unit that contains a sample; and a microchip that includes at least: a sample inlet into which the sample is introduced; a sample flow path through which the sample introduced from the sample inlet flows; and a sorting flow path in which a target sample is sorted out from the sample, in which a first tube is inserted into and fixed to the sample inlet, in which the containing unit and the microchip are hermetically connected.

In the sample sorting kit according to the present technology, in the microchip, a second tube may be further fixed to an end of the first tube, the end being on a side where the first tube is not fixed to the sample inlet, and the containing unit may be hermetically connected via the second tube.

Furthermore, the sample sorting kit according to the present technology may further include: a reservoir unit that contains the target sample that has been sorted out, in which, in the microchip, a third tube may be inserted into and fixed to an outlet of the sorting flow path, and the reservoir unit may be hermetically connected via the third tube.

Moreover, the sample sorting kit according to the present technology may further include: a disposal unit into which the sample other than the target sample is discarded, in which the microchip may further include a disposal flow path through which the sample other than the target sample is discarded, and a fourth tube may be inserted into and fixed to an outlet of the disposal flow path, and the disposal unit may be hermetically connected via the fourth tube.

In addition, the sample sorting kit according to the present technology may further include: a sheath fluid containing unit that contains a sheath fluid, in which the microchip may further include: a sheath fluid inlet into which a sheath fluid is introduced; and a sheath flow path through which the sheath fluid introduced from the sheath fluid inlet flows, and a fifth tube may be inserted into and fixed to the sheath fluid inlet, and the sheath fluid containing unit may be hermetically connected via the fifth tube.

Furthermore, the sample sorting kit according to the present technology may further include: a gate fluid containing unit that contains a gate fluid, in which the microchip may further include: a gate fluid inlet into which a gate fluid is introduced; and a gate flow path through which the gate fluid introduced from the gate fluid inlet flows, and a sixth tube may be inserted into and fixed to the gate fluid inlet, and the gate fluid containing unit may be hermetically connected via the sixth tube.

In the present technology, "microparticles" may broadly include biologically relevant microparticles such as cells, microorganisms, and liposomes, synthetic particles such as latex particles, gel particles, and industrial particles, and the like.

The biologically relevant microparticles include chromosomes, liposomes, mitochondria, organelles (cellular organelles), and the like that are included in various cells. The cells include animal cells (hematopoietic cells and the like, for example) and plant cells. The microorganisms include bacteria such as *Escherichia coli*, viruses such as tobacco mosaic virus, fungi such as yeast, and the like. Moreover, the biologically relevant microparticles also include biologically relevant polymers such as nucleic acids, proteins, and complexes thereof. Furthermore, the industrial particles may be, for example, organic or inorganic polymer materials, metals, or the like. The organic polymer materials include polystyrene, styrene-divinylbenzene, polymethyl methacrylate, and the like. The inorganic polymer materials include glass, silica, magnetic materials, and the like. The metals include gold colloid, aluminum, and the like. These microparticles generally have spherical forms, but in the present technology, they may be non-spherical and their sizes, masses, and the like are not particularly limited.

Effects of the Invention

According to the present technology, a technology capable of preventing a sample from being retained can be provided in the present technology.

Note that the effects described above are not restrictive, and any of effects described in the present disclosure may be included.

MODE FOR CARRYING OUT THE INVENTION

A preferred mode for carrying out the present technology will now be described with reference to the drawings.

The embodiment described below shows an example of representative embodiments of the present technology, and the scope of the present technology is not construed as being limited by the embodiment. Note that descriptions will be provided in the order mentioned below.

1. Microchip 1
2. Sample Sorting Kit 100
   (1) Microchip 1
   (2) Containing unit 2
   (3) Reservoir unit 3
   (4) Disposal unit 4
   (5) Sheath fluid containing unit 5
   (6) Gate fluid containing unit
   (7) Sealing unit 6
   (8) Others 3. Sample Sorting Apparatus A
   (1) Sample sorting kit 100
   (2) Light irradiation unit 101
   (3) Light detection unit 102
   (4) Computation unit 103
   (5) Position control unit 104
   (6) Agent input management unit 105
   (7) Culture unit 106
   (8) Pressure adjustment unit 107

1. Microchip 1

The microchip 1 includes at least a sample inlet 11 into which a sample is introduced, a sample flow path 12 through which the sample introduced from the sample inlet 11 flows, and a sorting flow path 16 in which a target sample is sorted out from the sample, and a first tube T1 is inserted into and fixed to the sample inlet 11. Furthermore, the microchip 1 may include any other flow path or tube as necessary. The following describes the microchip 1 in detail.

Figure 12:
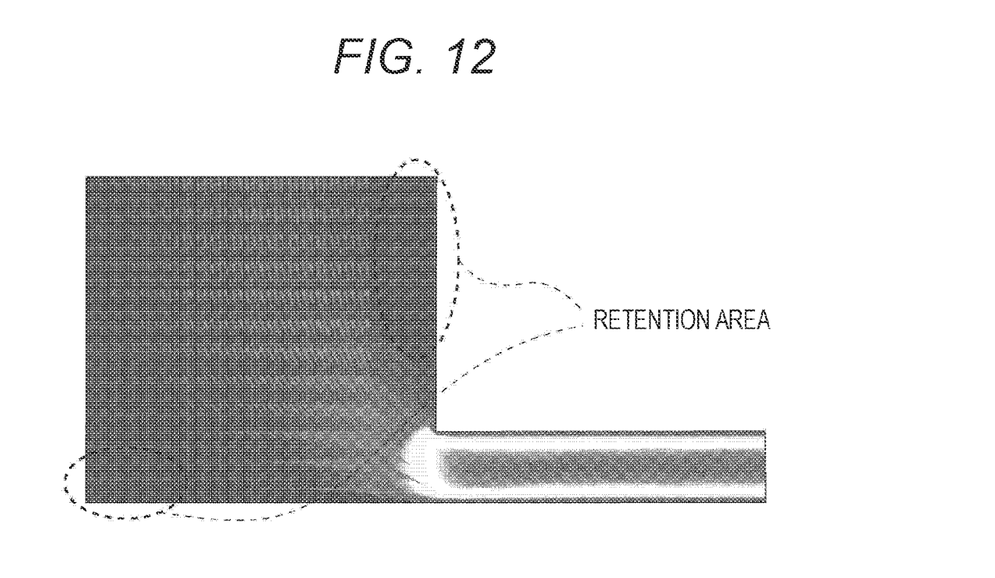
FIG. 12 is a diagram illustrating a velocity vector of a flow path in a case of employing a structure in which the chip is connected to an external flow path via a conventional manifold.

FIG. 12 is a diagram illustrating a velocity vector of a flow path in a case of employing a structure in which the chip is connected to an external flow path via a conventional manifold. In a case where this structure is employed, it is necessary to have a flow path that bends approximately 90 degrees in the middle, with the result that an area retaining a sample is extensively created to cause a sample to be retained in the area as illustrated in FIG. 12, posing a problem of crocking or the like.

Figure 2:
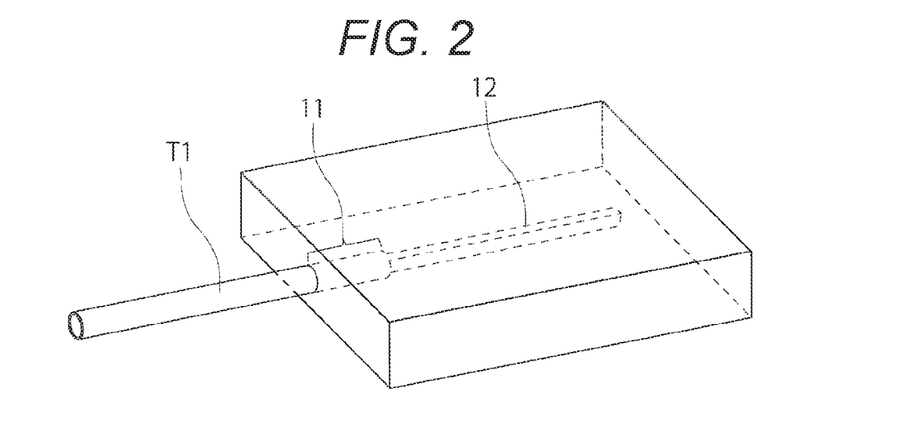
FIG. 2 is a perspective view schematically illustrating an example of a structure around a sample inlet of the microchip according to the present technology.
Figure 3:
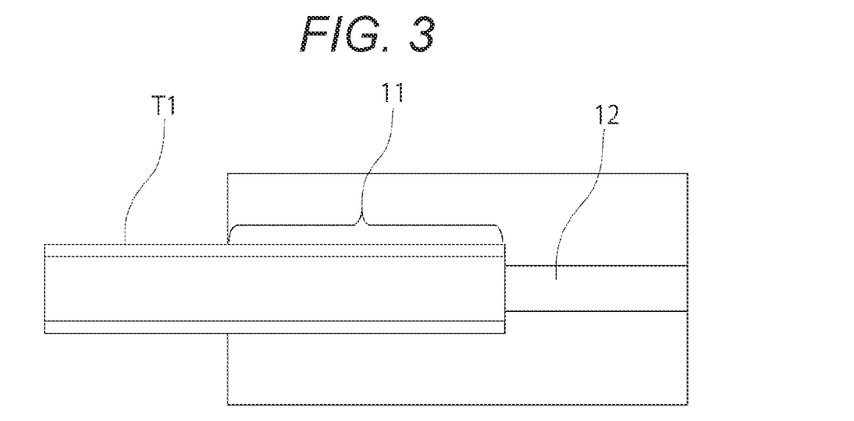
FIG. 3 is a cross-sectional view schematically illustrating an example of a structure around the sample inlet of the microchip according to the present technology.
Figure 4:
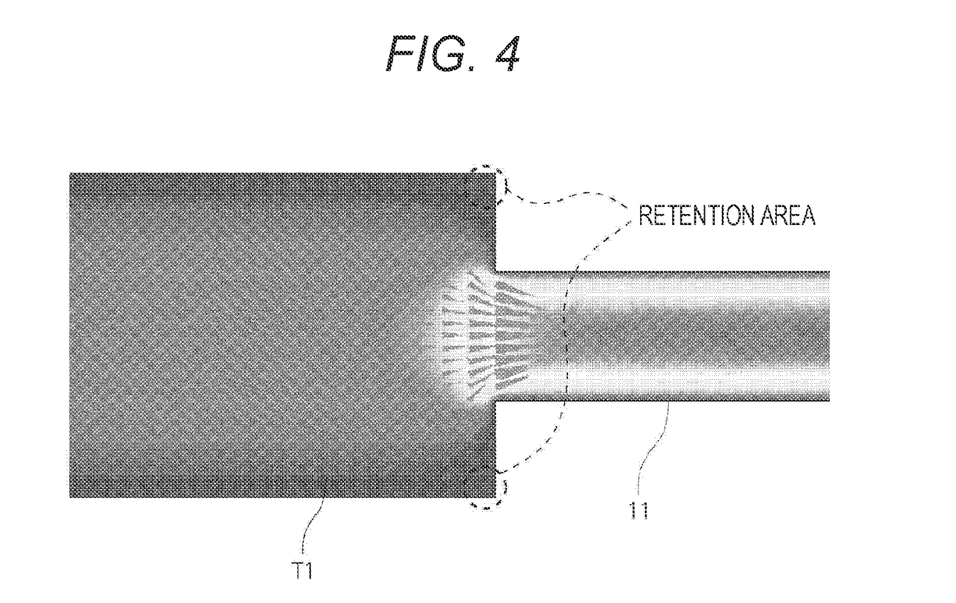
FIG. 4 is a diagram illustrating a velocity vector of a flow path in the sample inlet and in a first tube.

On the other hand, the sample inlet 11 of the microchip 1 according to the present technology has the first tube T1 inserted therein and fixed as illustrated in the figures including FIGS. 2, 3, and the like, so that no flow path bends with respect to the sample line. Thus, as illustrated in FIG. 4, an area retaining samples is smaller, making it possible to suppress the phenomenon in which samples are deposited in an area having a velocity field of 0.

In the present technology, the first tube T1 is preferably fixed coaxially with the sample flow path 12, as illustrated in the figures including FIGS. 2, 3, and the like. As a result, samples can be further prevented from being retained.

In addition, in the present technology, the method for fixing the first tube T1 to the sample inlet 11 is not particularly limited, and examples of the method include mechanical fitting, chemical joining, and so on. Among other methods, in the present technology, the tube can be fixed with an adhesive agent, for example. Fixing the tube by using this method can reduce the cost of manufacturing the microchip 1. In a case where the tube is fixed with an adhesive agent, the first tube T1 may be, for example, a PEEK tube or the like.

Figure 5:
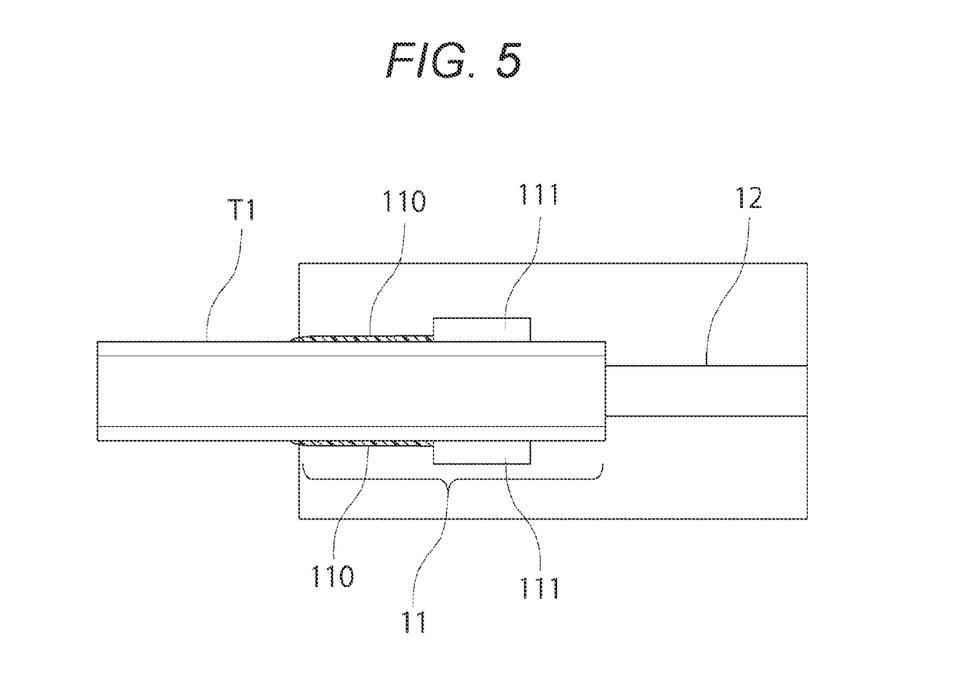
FIG. 5 is a cross-sectional view schematically illustrating an example of a structure around the sample inlet of the microchip according to the present technology, the structure being different from the structure in FIG. 3.

In this case, it is preferable that the sample inlet 11 is provided with an abrupt expansion flow path 111 having a larger volume than the volume of the sample flow path 12, as illustrated in FIG. 5. In a case where an adhesive agent is used to fix the tube, there is a possibility that the adhesive agent flows around due to a capillary action and fills the flow path. When the phenomenon occurs, the flow path in the microchip is filled up, failing to function as a flow path. In contrast, providing the abrupt expansion flow path 111 makes it possible to suppress the phenomenon in which the adhesive agent 110 flows around due to a capillary action.

The shape and the like of the abrupt expansion flow path 111 are not particularly limited. Furthermore, the volume of the abrupt expansion flow path 111 is preferably equal to or greater than $\pi\varphi^2 L/4$ m$^3$, where $\varphi$ is the outer diameter of the first tube T1 and L is the length of the first tube T1. As a result, it is made possible to further suppress the phenomenon in which the adhesive agent flows around due to a capillary action.

Furthermore, as illustrated in FIG. 5, the abrupt expansion flow path 111 is preferably located upstream of an end of the sample inlet 11, the end being on the side where the first tube T1 is fixed. As a result, it is made possible to further suppress the phenomenon in which the adhesive agent flows around due to a capillary action.

Figure 6:
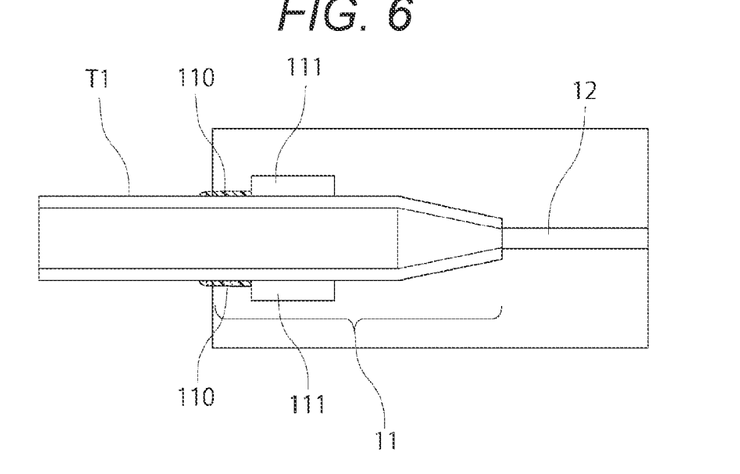
FIG. 6 is a cross-sectional view schematically illustrating an example of a structure around the sample inlet of the microchip according to the present technology, the structure being different from the structures in FIGS. 3 and 5.

In the present technology, as illustrated in FIG. 6, an end of the sample inlet 11, the end being on the side where the first tube T1 is fixed, and an end of the first tube T1, the end being on the side where the first tube T1 is fixed to the sample inlet 11, may be tapered. As a result, the sample flow path 12 can be centered with higher accuracy.

Figure 7:
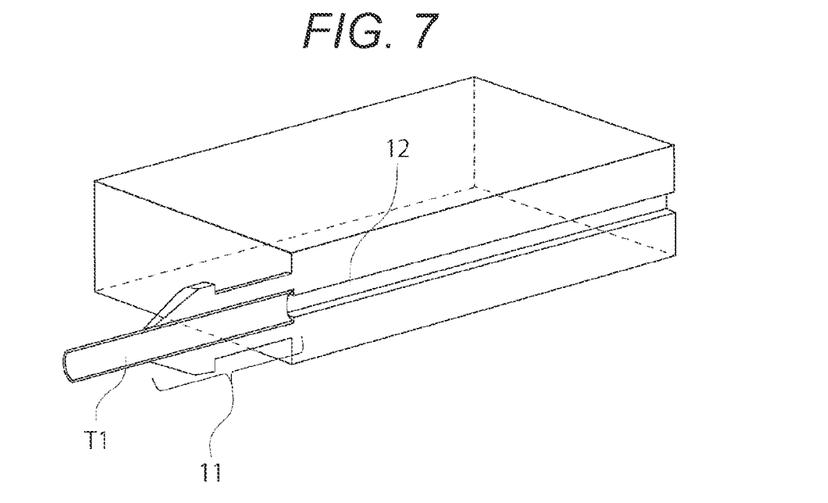
FIG. 7 is a perspective view schematically illustrating an example of a structure around the sample inlet of the microchip according to the present technology, the structure being different from the structures in FIGS. 3, 5, and 6.

Furthermore, as illustrated in FIG. 7, the microchip 1 according to the present technology may have a structure for inserting the first tube T1 into an end of the chip.

Figure 8:
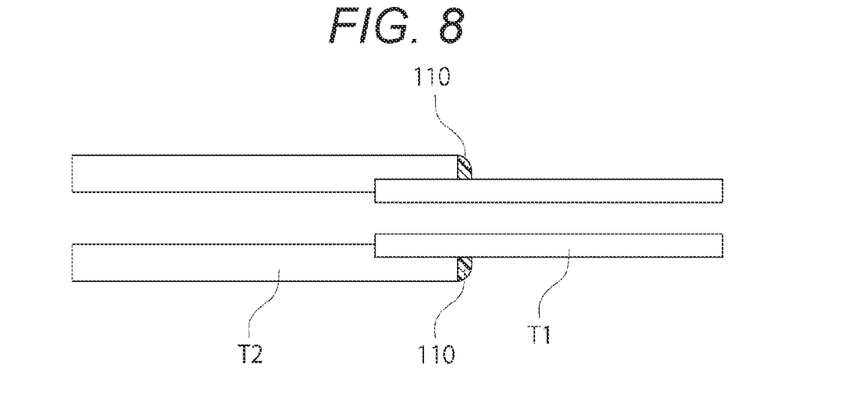
FIG. 8 is a schematic diagram schematically illustrating an example of a structure in which a second tube is fixed to the first tube.

Furthermore, in the present technology, a second tube T2 may be further fixed to an end of the first tube T1, the end being on the side where the first tube T1 is not fixed to the sample inlet 11. In this case, for example, the second tube T2 is inserted into the first tube T1, and the periphery thereof, an end of the first tube T1, and the like are fixed with the adhesive agent 110 as illustrated in FIG. 8, so as to have a structure in which flow paths are arranged along the same straight line. Employing such structure makes it possible to change the material of the tube without using a connector or the like. Then, furthermore, the fixing of the two tubes may be reinforced by utilizing amine linkage or the like. Examples of a method for promoting amine linkage may include using PPX (manufactured by Cemedine Co., Ltd.) and the like. Moreover, in a case where the two tubes T1 and T2 are fixed with an adhesive agent as described above, the second tube T2 may be, for example, a PVC tube having a Shore hardness of 65 or less, and the like. Furthermore, the joining strength can be increased by further stacking a PVC tube or the like having a larger inner diameter on the outer surface of the portion where the tube T1 and the tube T2 are fixed.

The following describes in detail the sorting by the microchip 1.

Figure 9:
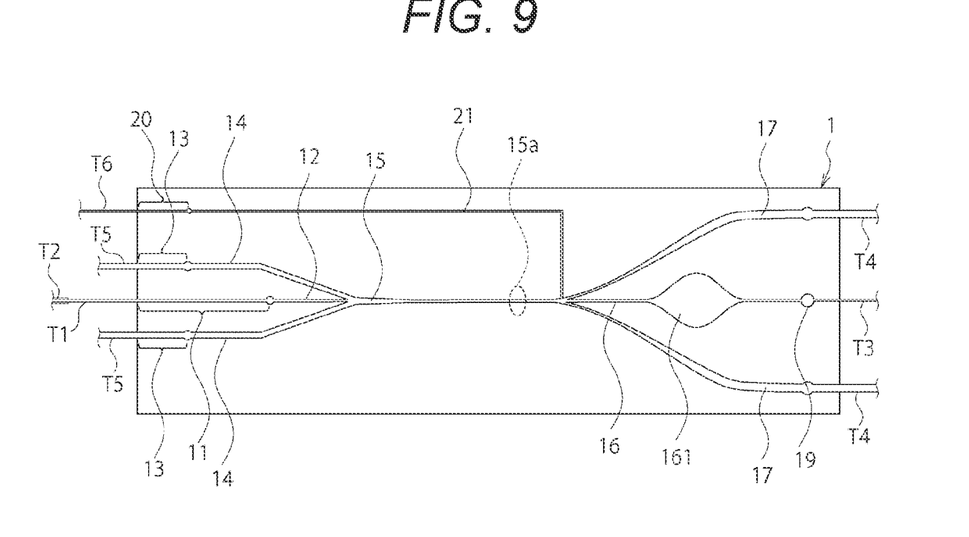
FIG. 9 is a front view schematically illustrating an example of an internal structure of the microchip according to the present technology.

FIG. 9 is a front view schematically illustrating an example of an internal structure of the microchip 1 according to the present technology. A sample that contains microparticles is introduced into the sample flow path 12 from the sample inlet 11. Furthermore, a sheath fluid is introduced from a sheath fluid inlet 13. The sheath fluid introduced from the sheath fluid inlet 13 is divided into two sheath flow paths 14 and 14 and delivered. The sample flow path 12 and the sheath flow paths 14 and 14 join together into the main flow path 15. The sample fluid laminar flow delivered through the sample flow path 12 and the sheath fluid laminar flows delivered through the sheath fluid paths 14 and 14 join together in the main flow path 15 to form a sheath flow in which the sample fluid laminar flow is sandwiched between the sheath fluid laminar flows.

The reference numeral 15a in FIG. 9 denotes a detection area that is irradiated with excitation light by a light irradiation unit 101, which is described later, so that fluorescence and scattered light are detected by a light detection unit 102. The microparticles, which are arranged in a line in the sheath flow formed in the main flow path 15, are delivered to the detection area 15a and irradiated with excitation light from the light irradiation unit 101.

The main flow path 15 is branched into three flow paths downstream of the detection area 15a. Downstream of the detection area 15*a*, the main flow path 15 communicates with the three branch flow paths, namely a sorting flow path 16 and disposal flow paths 17 and 17. Among these flow paths, the sorting flow path 16 is the flow path into which a sample determined to have a predetermined optical characteristic (also referred to as a "target sample") is taken. On the other hand, a sample determined not to have a predetermined optical characteristic (also referred to as "non-target sample") flows into either one of the two disposal flow paths 17 and 17 without being taken into the sorting flow path 16.

The target sample is taken into the sorting flow path 16 by using a piezoelectric element such as a piezo element to generate a negative pressure in the sorting flow path 16 and, with the help of the negative pressure, sucking the sample including a target sample and the sheath fluid into the sorting flow path 16. The piezoelectric element is disposed in contact with a surface of the microchip 1 at a position corresponding to the sorting flow path 16. More specifically, the piezoelectric element is disposed at a position corresponding to a pressure chamber 161 provided as a region where an inner space in the sorting flow path 16 is expanded.

The inner space of the pressure chamber 161 is expanded in the planar direction (the width direction of the sorting flow path 16) as illustrated in FIG. 9, and also expanded in the cross-sectional direction (the height direction of the sorting flow path 16). That is, the sorting flow path 16 is expanded both in the width direction and in the height direction in the pressure chamber 161. In other words, the sorting flow path 16 is formed to have, at the pressure chamber 161, an expanded cross section perpendicular to the direction in which the sample and the sheath fluid flow.

The piezoelectric element generates an expansion and contraction force in accordance with a change in the applied voltage to cause a pressure change in the sorting flow path 16 via the surface (contact surface) of the microchip 1. When a flow occurs in the sorting flow path 16 due to a pressure change in the sorting flow path 16, the volume in the sorting flow path 16 changes at the same time. The volume in the sorting flow path 16 changes until the volume reaches a volume defined by the displacement amount of the piezoelectric element corresponding to the applied voltage. More specifically, when the piezoelectric element is expanded with a voltage applied thereto, the piezoelectric element presses the displacement plate included in the pressure chamber 161 to keep the volume of the pressure chamber 161 small. Then, when the applied voltage is reduced, the piezoelectric element generates a force in a contracting direction to reduce the pressure applied to the displacement plate, thereby generating a negative pressure in the pressure chamber 161.

In the present technology, in order to efficiently transmit the expansion and contraction force of the piezoelectric element to the pressure chamber 161, it is preferable that the surface of the microchip 1 is recessed at a position corresponding to the pressure chamber 161 and the piezoelectric element is disposed in the recess. As a result, the displacement plate serving as the contact surface of the piezoelectric element can be made thinner, and the displacement plate can be easily displaced with a change in the pressing force caused by the expansion or contraction of the piezoelectric element to cause the volume of the pressure chamber 161 to vary.

Then, the target sample delivered through the sheath flow formed in the main flow path 15 is taken into the sorting flow path 16 from the communication port.

The microchip 1 is made by sticking together substrate layers on which the sample flow path 12, the sorting flow path 16, and the like are formed. The sample flow path 12, the sorting flow path 16, or the like can be formed on a substrate layer by injection molding of a thermoplastic resin using a mold. Examples of the thermoplastic resin that can be employed include plastics conventionally known as materials of microchips, such as polycarbonate, polymethyl methacrylate (PMMA), cyclic polyolefin, polyethylene, polystyrene, polypropylene, and polydimethylsiloxane (PDMS). Note that the number of substrate layers included in the microchip 1 is not particularly limited, and the microchip 1 may include, for example, two or more layers.

In the present technology, a third tube T3 may be inserted into and fixed to the outlet of the sorting flow path 16, as illustrated in FIG. 9. As a result, the need to employ a structure in which the chip is connected to an external flow path via a manifold is eliminated, flow paths being bent are absent, and an area retaining target samples is smaller, making it possible to suppress the phenomenon in which target samples are deposited in an area having a velocity field of 0. That is, the target sample that has been sorted out can be prevented from being retained.

Furthermore, in a case where the microchip 1 according to the present technology further includes disposal flow paths 17 and 17 through which a sample (non-target sample) other than the target sample is discarded, a fourth tube T4 may be inserted into and fixed to each of the outlets of the disposal flow paths 17 and 17. As a result, non-target samples can be discharged out of flow paths of the microchip 1 without passing through another member or the like, thus improving the usability.

Moreover, in a case where the microchip 1 according to the present technology further includes a sheath fluid inlet 13 into which the sheath fluid is introduced and a sheath flow paths 14 and 14 through which the sheath fluid introduced from the sheath fluid inlet 13 flows, a fifth tube T5 may be inserted into and fixed to the sheath fluid inlet 13, as illustrated in FIG. 9. As a result, the sheath fluid can be introduced into the sheath fluid inlet 13 without passing through another member or the like, thus improving the usability.

Furthermore, the microchip 1 according to the present technology may further include a gate fluid inlet 20 into which a gate fluid is introduced and a gate flow path 21 along which the gate fluid introduced from the gate fluid inlet 20 flows. In this case, a sixth tube T6 may be inserted into and fixed to the gate fluid inlet 20 as illustrated in FIG. 9. As a result, the gate fluid can be introduced into the gate fluid inlet 20 without passing through another member or the like, thus improving the usability.

The "gate flow path" is at least one flow path connected to, or provided to, for example, intersect orthogonally with, the sorting flow path 16 running from the three branch flow paths, namely the sorting flow path 16 and the disposal flow paths 17 and 17 to a point immediately before the pressure chamber 161, for example. The "gate fluid" refers to a fluid that is flowed through the gate flow path and serves as a main solvent for the sample such as microparticles that have been sorted out and collected. Therefore, any of a variety of fluids can be selected as the gate fluid in accordance with the intended use. For example, in a case where the fluid medium used as a microparticles-containing fluid, the sheath fluid, or the microparticles are proteins, a fluid suitable for the microparticles, such as a buffer solution whose pH or the like is adjusted and containing a surfactant, can be flowed at a certain flow rate.

In particular, in a case where the microparticles are cells, a cell culture solution, a cell preservation solution, or the like can be used as the gate fluid. In the case of using a cell culture solution, the cell culture solution is suitable for the subsequent step to be carried out on the cells that have been sorted out and collected, such as, for example, cell culture, cell activation, gene transfection, or any other similar step. In the case of using a cell preservation solution, the cell preservation solution is suitable for preserving and transporting the cells that have been collected. Furthermore, in a case where the cells to be sorted out and collected are undifferentiated cells such as iPS cells, a differentiation inducing solution can be used to perform the subsequent work efficiently.

Note that any of a variety of fluids can also be selected as the sheath fluid. A flow made up of a gate fluid is herein referred to as a "gate flow".

Upstream of the gate flow path 21, a fluid is introduced independently of the gate flow inlet 20 and is allowed to flow at an appropriate flow rate. In the present technology, a fluid is introduced into the gate flow path 21 at a lower flow rate than the flow rate of a fluid introduced into the sheath flow paths 14 and 14. Therefore, the present technology is economical in a case where an expensive fluid such as a cell culture solution, a cell preservation solution, or a differentiation inducing solution is used in the gate flow path 21 only.

Furthermore, the gate flow may be generated by branching off from the sheath fluid flow. For example, the sheath flow paths 14 and 14 following the sheath fluid inlet and the upstream end of the gate flow path 21 may be connected so that the sheath fluid flow is allowed to branch off and partly flow into the gate flow path 21 to form the gate flow. In this case, it is necessary to appropriately design the flow path resistance of the gate flow path 21 so that the gate flow has an appropriate flow rate.

At an intersection between the gate flow path 21 and the sorting flow path 16, there are created a gate flow moving straight along the gate flow path 21 and a gate flow moving toward the detection area 15a side and the pressure chamber 161 side. With the latter gate flow, the microparticles not to be obtained (non-target samples) can be prevented from entering the sorting flow path 16 toward the pressure chamber 161 side. The gate flow flowing through the gate flow path 21 flows out to the sorting flow path 16, and branches into a gate flow toward the detection area 15a side of the sorting flow path 16 and a gate flow toward the pressure chamber 161 side of the sorting flow path 16. With the former gate flow, non-target samples can be prevented from entering the sorting flow path 16 toward the pressure chamber 161 side.

A containing unit 2 described later and others may be connected to the microchip 1 according to the present technology, and the microchip 1 may be distributed as a part of an article such as a cartridge, a unit, a device, a kit, or an instrument for a closed-type cell sorter. In addition, according to the present technology 2. Sample Sorting Kit 100

Figure 1:
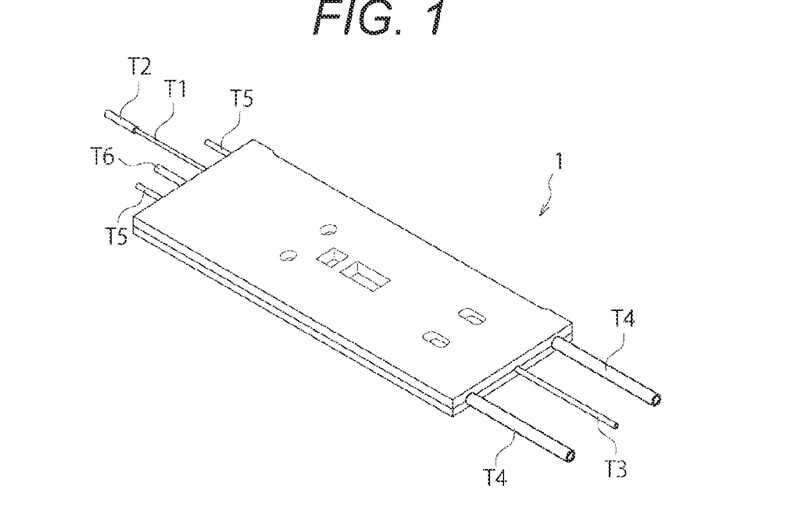
FIG. 1 is a perspective view illustrating an example of an embodiment of a microchip according to the present technology.
Figure 10:
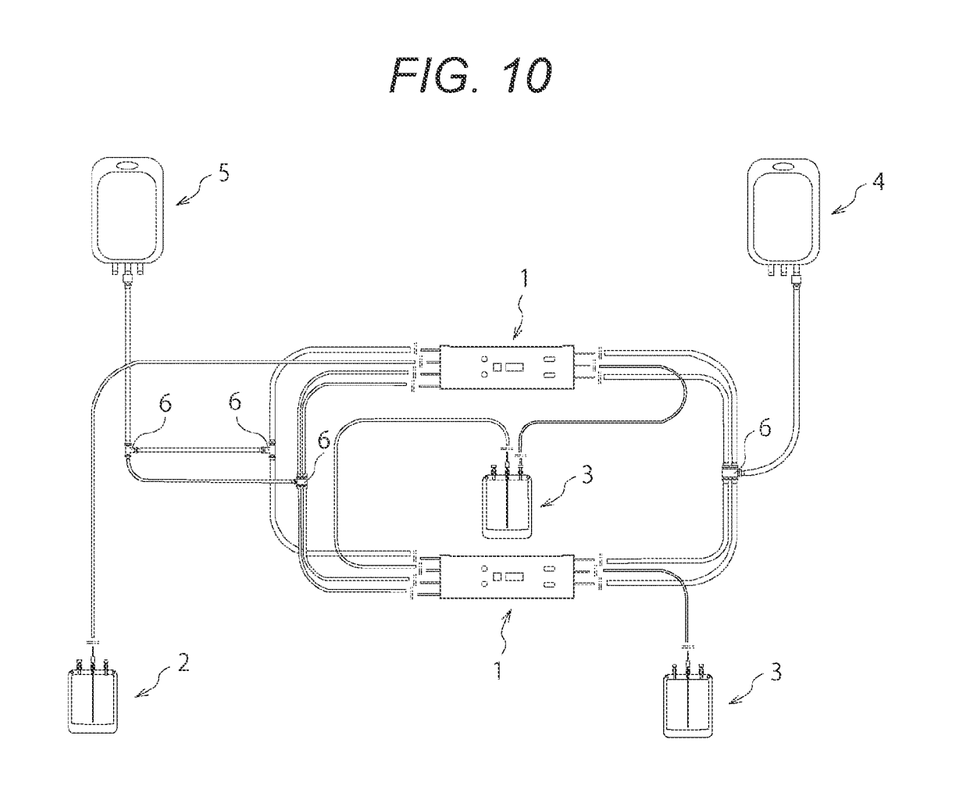
FIG. 10 is a diagram schematically illustrating an example of an embodiment of a sample sorting kit according to the present technology, the sample sorting kit employing the microchip according to an embodiment as illustrated in FIG. 1.

FIG. 10 is a diagram schematically illustrating an example of an embodiment of a sample sorting kit 100 according to the present technology, the sample sorting kit 100 employing the microchip according to an embodiment as illustrated in FIG. 1. The sample sorting kit 100 includes at least a containing unit 2 in which a sample is contained and a microchip 1, and the containing unit 2 and the microchip 1 are hermetically connected. Furthermore, other units may be included as necessary.

The sample sorting kit 100 according to the present technology includes the containing unit 2 and the microchip 1, and if necessary, a reservoir unit 3, a disposal unit 4, a sheath fluid containing unit 5, a gate fluid containing unit, and the like, which are hermetically connected. Therefore, target samples can be sorted out and stored in sealed spaces, and thus target samples can be sorted out at higher purity. Furthermore, contamination of the sample sorting kit itself with the mist containing a target sample and/or mixing of a sorted-out target sample with other substances can be prevented. As a result, the sample sorting kit 100 according to the present technology can even be used for clinical applications such as immune cell therapy in which pure target samples are required.

Furthermore, the sample sorting kit 100 itself according to the present technology can be made disposable so as to avoid the risk and the like of contamination between samples, thereby improving the usability.

The following describes in detail the individual units included in the sample sorting kit 100.

(1) Microchip 1

The sample sorting kit 100 includes the microchip 1. The microchip 1 is similar to the microchip described above, and thus description thereof is omitted here.

(2) Containing Unit 2

The containing unit 2 contains a sample to be sorted out by the microchip 1. The containing unit 2 may include, for example, a cylindrical tubular body that has one end opened and a lid portion that is fitted to the tubular body and blocks the opened end. In addition, a plurality of opening valves for containing a sample in the cylindrical body is formed in the lid portion, and each of the opening valves employs a check valve configuration. Therefore, in the state where the sample is contained in the containing unit 2 with the opening valves, the sample is prevented from coming out of the containing unit 2. Furthermore, the sample is sealed off from the external atmosphere by the opening valve configuration.

Samples are not particularly limited; as long as samples include a target sample to be sorted out by using the sample sorting kit 100 according to the present technology, no specific limitation is imposed on the samples. Specifically, examples thereof include cells derived from a patient, and the like, such as whole blood, peripheral blood mononuclear cells contained in whole blood, and a cell suspension containing lymphocytes only.

In the present technology, in a case where the second tube T2 is further fixed to an end of the first tube T1 in the microchip 1, the end being not fixed to the sample inlet 11, the containing unit 2 may be hermetically connected via the second tube T2. As a result, it is made possible to avoid forming a bent flow path in the sample line to prevent samples from being retained. Furthermore, the risk of contamination and the like can be avoided, thereby improving the usability.

(3) Reservoir Unit 3

The sample sorting kit 100 according to the present technology may include the reservoir unit 3 as necessary. The reservoir unit 3 contains a target sample that has been sorted out. The reservoir unit 3 is formed, for example, in a bag shape to contain a target sample, and includes an opening valve connected to the sorting flow path terminal 19 of the microchip 1 via a sealing unit 4, which is described later. The opening valve employs a so-called check valve configuration, and in the state where a target sample is contained in the reservoir unit 3 with the opening valve, the target sample is prevented from being coming out of the reservoir unit 3. Furthermore, the target sample is prevented from being exposed to the external atmosphere by the opening valve configuration.

The above-described configuration of the reservoir unit 3 is merely an example, and any known configuration may be employed as long as the target sample is prevented from being exposed to the external atmosphere.

In the present technology, in a case where the third tube T3 is inserted into and fixed to the outlet of the sorting flow path 16 in the microchip 1, the reservoir unit 3 may be hermetically connected via the third tube T3. As a result, it is made possible to avoid forming a bent flow path in the target sample line to prevent target samples from being retained. Furthermore, the risk of contamination and the like can be avoided, thereby improving the usability.

Note that, in the sample sorting kit 100 according to the present technology, a sample may be further sorted out from the target sample contained in the reservoir unit 3 by using the microchip 1, as illustrated in FIG. 10. In this case, the sample that has been further sorted out may be contained in the reservoir unit 3 via the third tube T3.

(4) Disposal Unit 4

In the sample sorting kit 100 according to the present technology, non-target samples need to be removed when a target sample is only sorted out from samples in the microchip 1. Furthermore, samples containing the target samples need to be removed because a sheath flow is formed on the microchip 1 to sort out a target sample. Therefore, the sample sorting kit 100 according to the present technology may include the disposal unit 4 as necessary. Samples other than target samples are discarded into the disposal unit 4.

In a case where the microchip 1 of the present technology further includes disposal flow paths 17 and 17 through which a sample (non-target sample) other than target samples is discarded and the fourth tube T4 is inserted into and fixed to each of the outlets of the disposal flow paths 17 and 17, the disposal unit 4 may be hermetically connected via the fourth tube T4. As a result, target samples can be sorted out and non-target samples can be discarded in sealed spaces including the disposal unit 4.

(5) Sheath Fluid Containing Unit 5

In the sample sorting kit 100 according to the present technology, a sheath flow is formed on the microchip 1 to sort out a target sample from samples. Therefore, the sample sorting kit 100 according to the present technology may include the sheath fluid containing unit 5 as necessary. A sheath fluid is contained in the sheath fluid containing unit 5.

The sheath fluid containing unit 5 includes, for example, a tubular member into which a sheath fluid flows, and the tubular member communicates with the sheath fluid inlet 13 in the microchip 1. As a result, the sheath fluid is allowed to flow into a flow path in the microchip 1 to form a sheath flow.

The configuration of the sheath fluid containing unit 5 is not particularly limited, and a known configuration may be employed. Furthermore, the configuration for discharging a sheath fluid from the sheath fluid containing unit 5 is not particularly limited. For example, a drive source such as an actuator may be used.

In the present technology, in a case where the microchip 1 further includes the sheath fluid inlet 13 into which a sheath fluid is introduced and the sheath flow paths 14 and 14 along which the sheath fluid introduced from the sheath fluid inlet 13 flows, and if the fifth tube T5 is inserted into and fixed to the sheath fluid inlet 13, the sheath fluid containing unit 5 may be hermetically connected via the fifth tube T5. As a result, introduction of a sheath fluid can also be completed in a sealed space, thereby improving the usability.

(6) Gate Fluid Containing Unit

Furthermore, the sample sorting kit 100 according to the present technology may include the gate fluid containing unit as necessary. A gate fluid is contained in the gate fluid containing unit. The "gate fluid" is similar to the gate fluid described above, and thus description thereof is omitted here.

In the present technology, in a case where the microchip 1 further includes the gate fluid inlet 20 into which a gate fluid is introduced and the gate flow path 21 along which the gate fluid introduced from the gate fluid inlet 20 flows, and if the sixth tube T6 is inserted into and fixed to the gate fluid inlet 20, the gate fluid containing unit may be hermetically connected via the sixth tube T6. As a result, containment of a gate fluid can also be completed in a sealed space, thereby improving the usability.

(7) Sealing Unit 6

The sample sorting kit 100 according to the present technology may include a sealing unit 6 as necessary. As illustrated in FIG. 10, by disposing the sealing unit 6, the individual units can be hermetically connected to each other and tubes having different inner diameters can be joined together via the sealing unit 6.

For example, the sealing unit 6 is roughly divided into a male member and a female member that is hermetically connected to the male member via a sealant. The connection strength between each of these members and each tube disposed on the microchip 1 can be reinforced with an adhesive or the like. Furthermore, in a case where an ultraviolet/visible light curable adhesive or the like is used as the adhesive, a stronger adhesive strength can be achieved by using a member including a nylon material having an amide bond. Note that the sealing unit 6 is not limited to this configuration, and a sealed structure usually used in a sample sorting kit (for example, a known aseptic connector or the like) can be employed. Furthermore, an alternative sealed structure may be provided in which a tubular member is protruded from each of the units described above, and the tubular members protruding from the individual units are heat-fused to each other so that the individual units are directly connected.

(8) Others

FIG. 10 shows an embodiment in which a plurality of microchips 1 is provided. However, in the sample sorting kit 100 according to the present technology, the number of the microchips 1, the containing units 2, the reservoir units 3, the disposal units 4, the sheath fluid containing units 5, the gate fluid containing units, the sealing units 6, or the like is not particularly limited, and these units may be connected as appropriate on an as-needed basis. Furthermore, in conjunction therewith, the number of the first tubes T1, the second tubes T2, the third tubes T3, the fourth tubes T4, the fifth tubes T5, or the sixth tubes T6 is not particularly limited.

3. Sample Sorting Apparatus A

Figure 11:
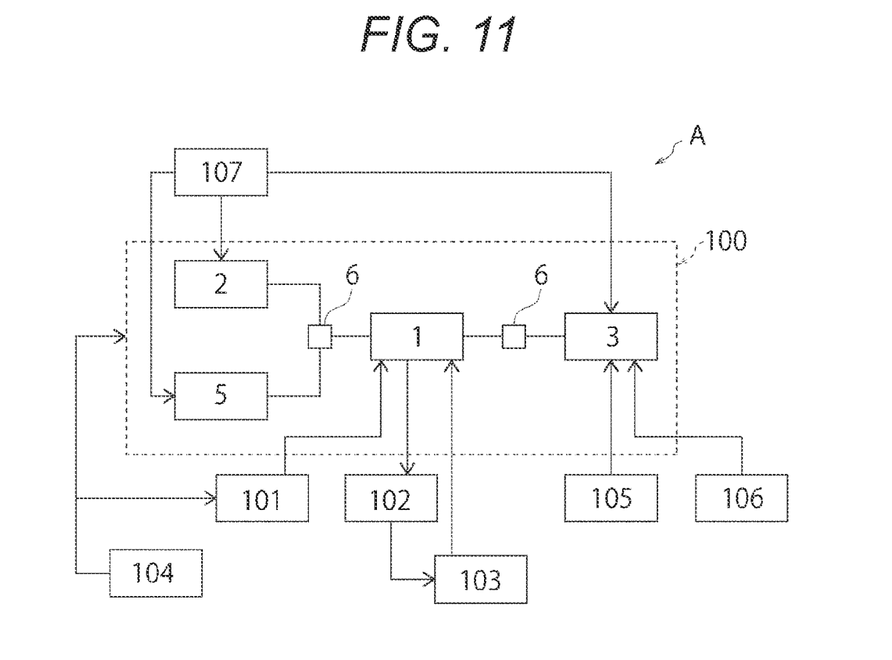
FIG. 11 is a diagram schematically illustrating an example of an embodiment of a sample sorting apparatus.

FIG. 11 is a diagram schematically illustrating an example of an embodiment of a sample sorting apparatus A. The following describes in detail an example configuration of the sample sorting apparatus A employing the microchip 1 and the sample sorting kit 100 according to the present technology.

(1) Sample Sorting Kit 100

The sample sorting apparatus A includes the sample sorting kit 100 that sorts out and stores target samples, for example. The sample sorting kit 100 includes the microchip 1. Note that the sample sorting kit 100 is similar to the sample sorting kit described above, and thus description thereof is omitted here.

(2) Light Irradiation Unit 101

The light irradiation unit 101 irradiates the samples to be sorted with light. Specifically, the light irradiation unit 101 irradiates, with light (excitation light), the samples flowing through the detection area 15*a* disposed on the main flow path 15 of the microchip 1.

The light irradiation unit 101 includes, for example, a light source that emits excitation light and an objective lens or the like that concentrates the excitation light on the samples flowing through the main flow path 15. The light source to be used may be appropriately selected from a laser diode, an SHG laser, a solid-state laser, a gas laser, a high-luminance LED, and the like depending on the purpose of analysis. Furthermore, if necessary, the light irradiation unit 101 may include an optical element other than the light source and the objective lens.

(3) Light Detection Unit 102

The light detection unit 102 detects the fluorescence and the scattered light emitted from the sample that has been irradiated with the excitation light for sorting. Specifically, the light detection unit 102 detects the fluorescence and the scattered light emitted from the sample and converts the detected fluorescence and scattered light into an electric signal. Then, the light detection unit 102 outputs the electric signal to the computation unit 103, which is described later.

The configuration of the light detection unit 102 is not particularly limited, and a known configuration may be employed. Likewise, the method for converting the light into an electric signal is not particularly limited.

(4) Computation Unit 103

The computation unit 103 receives an input of the electric signal produced through conversion in the light detection unit 102. Specifically, the computation unit 103 determines optical characteristics of samples and a target sample included in the samples on the basis of the input electric signal.

Moreover, the computation unit 103 includes a gating circuit for calculating a threshold to be used for sorting out a target sample from the samples, a threshold to be used for determining whether or not at least a required number of target samples have been sorted out, and the like. When a threshold for sorting out a target sample from the samples has been calculated in the gating circuit as configured above, the threshold is converted into an electric signal for sorting, and the sorting signal is output to the piezoelectric element included in the microchip 1.

Note that the configuration of the computation unit 103 is not particularly limited, and a known configuration may be employed. Moreover, a known method may be employed as the method for calculation carried out in the gating circuit of the computation unit 103.

(5) Position Control Unit 104

In a case where the microchip 1 is in the above-described configuration, the excitation light needs to be emitted onto the detection area 15*a* in the microchip 1. The position control unit 104 controls the relative positional relationship between the sample sorting kit 100 and the light irradiation unit 101.

The configuration of the position control unit 104 is not particularly limited, and a known configuration may be employed. Specifically, for example, an actuator or the like serving as a drive source may be included.

(6) Agent Input Management Unit 105

The target sample stored in the reservoir unit 3 in the sample sorting kit 100 may need to be activated or gene-transfected as necessary. The agent input management unit 105 inputs an agent for activating the target sample or an agent for gene-transfecting the target sample to the reservoir unit 3. Furthermore, the agent input management unit 105 manages the input amount and the like of each agent in accordance with the condition of the stored target sample.

Examples of the agent that can be used for activation include known agents such as various cytokines (for example, interleukin-2 (IL-2), IL-7, IL-15, IL-21, and the like) and various antibodies (for example, anti-CD3 antibodies, anti-CD28 antibodies, and the like), and examples of the agent that can be used for gene transfection include known agents such as various virus vectors into which a plasmid expressing a target gene is introduced (for example, adeno-associated virus vectors, adenovirus vectors, retrovirus vectors, lentivirus vectors, and the like). An appropriate agent can be selected in accordance with the type and condition of the stored target sample. Furthermore, a plurality of different known agents can be used in combination.

(7) Culture Unit 106

Depending on the intended use of the sample sorting apparatus A, the quantity of a target sample that has been sorted out by the sample sorting kit 100 may need to be increased. That is, the culture unit 106 cultures the target sample stored in the reservoir unit 3. Specifically, the culture unit 106 controls the temperature in the reservoir unit 3 to increase the quantity of the target sample contained in the reservoir unit 3.

Note that the method for adjusting the temperature in the culture unit 106 is not particularly limited, and a known method may be employed. For example, the reservoir unit 3 may include a heating element, and the culture unit 106 may output an electric signal to the heating element so as to control the temperature to rise/drop.

(8) Pressure Adjustment Unit 107

Since the containing unit 2, the microchip 1, the reservoir unit 3, and the like in the sample sorting kit 100 are hermetically connected to each other, a pressure change in the reservoir unit 3 may cause a pressure change in the containing unit 2 and/or the microchip 1. For this reason, the pressure adjustment unit 107 adjusts the pressure in the reservoir unit 3. More specifically, the pressure adjustment unit 107 is configured to generate a negative pressure in the reservoir unit 3, and may include, for example, a piezoelectric element such as a piezo element.

Moreover, the pressure adjustment unit 107 is preferably configured to adjust the pressure in the containing unit 2 by adjusting the flow rate of samples flowing out of the containing unit 2. In addition, the pressure adjustment unit 107 is preferably configured to adjust the pressure in the sheath fluid containing unit 5 by adjusting the flow rate of a sheath fluid flowing out of the sheath fluid containing unit 5.

Note that the present technology may have the following configurations.

(1)

A microchip including at least:

a sample inlet into which a sample is introduced;

a sample flow path through which the sample introduced from the sample inlet flows; and a sorting flow path in which a target sample is sorted out from the sample, in which a first tube is inserted into and fixed to the sample inlet.

(2)

The microchip according to (1), in which the first tube is fixed coaxially with the sample flow path.

(3)

The microchip according to (1) or (2), in which the first tube is fixed with an adhesive agent.

(4)
The microchip according to (3), in which the sample inlet is provided with an abrupt expansion flow path having a larger volume than the volume of the sample flow path.

(5)
The microchip according to (4), in which the volume of the abrupt expansion flow path is equal to or greater than $\pi \varphi^2 L/4$ m$^3$, where $\varphi$ is an outer diameter of the first tube and L is a length of the first tube.

(6)
The microchip according to (4) or (5), in which the abrupt expansion flow path is provided upstream of an end of the sample inlet, the end being on a side where the first tube is fixed.

(7)
The microchip according to any one of (1) to (6), in which an end of the sample inlet, the end being on a side where the first tube is fixed, and an end of the first tube, the end being on a side where the first tube is fixed to the sample inlet, are tapered.

(8)
The microchip according to any one of (1) to (7), in which a second tube is further fixed to an end of the first tube, the end being on a side where the first tube is not fixed to the sample inlet.

(9)
The microchip according to any one of (1) to (8), in which a third tube is inserted into and fixed to an outlet of the sorting flow path.

(10)
The microchip according to any one of (1) to (9), further including:
a disposal flow path through which a sample other than the target sample is discarded, in which
a fourth tube is inserted into and fixed to an outlet of the disposal flow path.

(11)
The microchip according to any one of (1) to (10), further including:
a sheath fluid inlet into which a sheath fluid is introduced; and
a sheath flow path through which the sheath fluid introduced from the sheath fluid inlet flows, in which
a fifth tube is inserted into and fixed to the sheath fluid inlet.

(12)
The microchip according to any one of (1) to (11), further including:
a gate fluid inlet into which a gate fluid is introduced; and
a gate flow path through which the gate fluid introduced from the gate fluid inlet flows, in which
a sixth tube is inserted into and fixed to the gate fluid inlet.

(13)
A sample sorting kit including at least:
a containing unit that contains a sample; and
a microchip that includes at least: a sample inlet into which the sample is introduced; a sample flow path through which the sample introduced from the sample inlet flows; and a sorting flow path in which a target sample is sorted out from the sample, in which a first tube is inserted into and fixed to the sample inlet, in which
the containing unit and the microchip are hermetically connected.

(14)
The sample sorting kit according to (13), in which
in the microchip, a second tube is further fixed to an end of the first tube, the end being on a side where the first tube is not fixed to the sample inlet, and
the containing unit is hermetically connected via the second tube.

(15)
The sample sorting kit according to (13) or (14), further including:
a reservoir unit that contains the target sample that has been sorted out, in which
in the microchip, a third tube is inserted into and fixed to an outlet of the sorting flow path, and
the reservoir unit is hermetically connected via the third tube.

(16)
The sample sorting kit according to any one of (13) to (15), further including:
a disposal unit into which the sample other than the target sample is discarded, in which
the microchip further includes a disposal flow path through which the sample other than the target sample is discarded, and a fourth tube is inserted into and fixed to an outlet of the disposal flow path, and
the disposal unit is hermetically connected via the fourth tube.

(17)
The sample sorting kit according to any one of (13) to (16), further including:
a sheath fluid containing unit that contains a sheath fluid, in which
the microchip further includes: a sheath fluid inlet into which a sheath fluid is introduced; and a sheath flow path through which the sheath fluid introduced from the sheath fluid inlet flows, and a fifth tube is inserted into and fixed to the sheath fluid inlet, and
the sheath fluid containing unit is hermetically connected via the fifth tube.

(18)
The sample sorting kit according to any one of (13) to (17), further including:
a gate fluid containing unit that contains a gate fluid, in which
the microchip further includes: a gate fluid inlet into which a gate fluid is introduced; and a gate flow path through which the gate fluid introduced from the gate fluid inlet flows, and a sixth tube is inserted into and fixed to the gate fluid inlet, and
the gate fluid containing unit is hermetically connected via the sixth tube.

REFERENCE SIGNS LIST

1 Microchip
2 Containing unit
3 Reservoir unit
4 Disposal unit
5 Sheath fluid containing unit
6 Sealing unit
11 Sample inlet
12 Sample flow path
13 Sheath fluid inlet
14 Sheath flow path
15 Main flow path
15a Detection area
16 Sorting flow path 17 Disposal flow path
18 Sheath fluid bypass flow path
19 Sorting flow path terminal
20 Gate fluid inlet
21 Gate flow path
161 Pressure chamber
111 Abrupt expansion flow path
110 Adhesive agent
100 Sample sorting kit
101 Light irradiation unit
102 Light detection unit
103 Computation unit
104 Position control unit
105 Agent input management unit
106 Culture unit
107 Pressure adjustment unit
A Sample sorting apparatus
T1 First tube
T2 Second tube
T3 Third tube
T4 Fourth tube
T5 Fifth tube
T6 Sixth tube

The invention claimed is:

1. A microchip, comprising:
a sample inlet into which a sample is introducible, wherein the sample inlet includes an abrupt expansion flow path;
a sample flow path, wherein the sample introduced from the sample inlet is flowable in the sample flow path;
a sorting flow path, wherein a target sample sorted out from the sample is flowable in the sorting flow path; and
a first tube fixed to the sample inlet, wherein a volume of the abrupt expansion flow path is equal to or greater than $\pi \varphi^2 L/4$ m$^3$, where o is an outer diameter of the first tube and L is a length of the first tube.

2. The microchip according to claim 1, wherein the first tube is coaxial with the sample flow path.

3. The microchip according to claim 1, wherein the first tube is fixed to the sample inlet with an adhesive agent.

4. The microchip according to claim 3, wherein the volume of the abrupt expansion flow path is larger than a volume of the sample flow path.

5. The microchip according to claim 4, wherein
the abrupt expansion flow path is upstream of an end of the sample inlet, and
the end of the sample inlet is on a side of the sample inlet where the first tube is fixed.

6. The microchip according to claim 1, wherein
each of the sample inlet and the first tube has a tapered end,
the tapered end of the sample inlet is on a side of the sample inlet where the first tube is fixed, and
the tapered end of the first tube is on a side of the first tube where the first tube is fixed to the sample inlet.

7. The microchip according to claim 1, further comprising a second tube fixed to a first end of the first tube,
wherein the first end of the first tube is opposite to a second end of the first tube that is fixed to the sample inlet.

8. The microchip according to claim 1, further comprising a third tube fixed to an outlet of the sorting flow path.

9. The microchip according to claim 1, further comprising:
a disposal flow path through which a non-target sample different from the target sample is discardable; and
a fourth tube fixed to an outlet of the disposal flow path.

10. The microchip according to claim 1, further comprising:
a sheath fluid inlet into which a sheath fluid is introducible;
a sheath flow path, wherein the sheath fluid introduced from the sheath fluid inlet is flowable in the sheath flow path; and
a fifth tube fixed to the sheath fluid inlet.

11. The microchip according to claim 1, further comprising:
a gate fluid inlet into which a gate fluid is introducible;
a gate flow path, wherein the gate fluid introduced from the gate fluid inlet is flowable in the gate flow path; and
a sixth tube fixed to the gate fluid inlet.

12. A sample sorting kit, comprising:
a containing unit configured to contain a sample; and
a microchip that comprises:
a sample inlet into which the sample is introducible, wherein the sample inlet includes an abrupt expansion flow path;
a sample flow path, wherein the sample introduced from the sample inlet is flowable in the sample flow path;
a sorting flow path, wherein a target sample sorted out from the sample is flowable in the sorting flow path; and
a first tube fixed to the sample inlet, wherein
a volume of the abrupt expansion flow path is equal to or greater than $\pi \varphi^2 L/4$ m$^3$, where o is an outer diameter of the first tube and L is a length of the first tube, and
the containing unit and the microchip are hermetically connected.

13. The sample sorting kit according to claim 12, wherein
the microchip further comprises a second tube fixed to a first end of the first tube,
the first end of the first tube is opposite to a second end of the first tube that is fixed to the sample inlet, and
the containing unit is hermetically connected to the microchip via the second tube.

14. The sample sorting kit according to claim 12, further comprising a reservoir unit configured to contain the target sample that has been sorted out, wherein
the microchip further comprises a third tube fixed to an outlet of the sorting flow path, and
the reservoir unit is hermetically connected to the microchip via the third tube.

15. The sample sorting kit according to claim 12, further comprising a disposal unit into which a non-target sample different from the target sample is discardable-discarded, wherein
the microchip further comprises:
a disposal flow path through which the non-target sample is discardable; and
a fourth tube fixed to an outlet of the disposal flow path, and
the disposal unit is hermetically connected to the microchip via the fourth tube.

16. The sample sorting kit according to claim 12, further comprising a sheath fluid containing unit configured to contain a sheath fluid, wherein
the microchip further comprises:
- a sheath fluid inlet into which the sheath fluid is introducible;
- a sheath flow path, wherein the sheath fluid introduced from the sheath fluid inlet is flowable in the sheath flow path; and
- a fifth tube fixed to the sheath fluid inlet, and
the sheath fluid containing unit is hermetically connected to the microchip via the fifth tube.

17. The sample sorting kit according to claim 12, further comprising a gate fluid containing unit configured to contain a gate fluid, wherein
the microchip further comprises:
- a gate fluid inlet into which the gate fluid is introducible;
- a gate flow path, wherein the gate fluid introduced from the gate fluid inlet is flowable in the gate flow path; and
- a sixth tube fixed to the gate fluid inlet, and
the gate fluid containing unit is hermetically connected to the microchip via the sixth tube.

\* \* \* \* \*